United States Patent
Makino

(10) Patent No.: US 9,492,481 B2
(45) Date of Patent: Nov. 15, 2016

(54) METHOD FOR PRODUCING BIOACTIVE AGENT, BIOACTIVE AGENT PRODUCED THEREBY, COSMETIC, FRESHNESS-MAINTAINING AGENT, GROWTH PROMOTION AGENT, SOIL CONDITIONING AGENT, AND PHARMACEUTICAL STOCK SOLUTION

(75) Inventors: Shinji Makino, Nishio (JP); Mie Makino, legal representative, Nishio (JP)

(73) Assignee: I.B.E. Co., Ltd., Aichi (JP)

(*) Notice: Subject to any disclaimer, the term of this patent is extended or adjusted under 35 U.S.C. 154(b) by 419 days.

(21) Appl. No.: 13/884,907

(22) PCT Filed: Nov. 12, 2010

(86) PCT No.: PCT/JP2010/070184
§ 371 (c)(1),
(2), (4) Date: Jun. 24, 2013

(87) PCT Pub. No.: WO2012/063357
PCT Pub. Date: May 18, 2012

(65) Prior Publication Data
US 2013/0287864 A1    Oct. 31, 2013

(51) Int. Cl.
| | | |
|---|---|---|
| *A61K 33/26* | (2006.01) |
| *A61K 8/19* | (2006.01) |
| *A61Q 19/00* | (2006.01) |
| *C05D 5/00* | (2006.01) |
| *C09K 17/40* | (2006.01) |
| *A23B 7/157* | (2006.01) |
| *A23L 3/358* | (2006.01) |
| *A61K 8/67* | (2006.01) |
| *A61K 31/122* | (2006.01) |
| *A61K 31/355* | (2006.01) |
| *A61K 31/375* | (2006.01) |

(52) U.S. Cl.
CPC ............... *A61K 33/26* (2013.01); *A23B 7/157* (2013.01); *A23L 3/358* (2013.01); *A61K 8/19* (2013.01); *A61K 8/676* (2013.01); *A61K 31/122* (2013.01); *A61K 31/355* (2013.01); *A61K 31/375* (2013.01); *A61Q 19/00* (2013.01); *C05D 5/00* (2013.01); *C09K 17/40* (2013.01); *A23V 2002/00* (2013.01); *A61K 2800/74* (2013.01)

(58) Field of Classification Search
CPC .......... A61K 8/19; A61K 33/26; A61Q 19/00; C05D 5/00; C09K 17/40
See application file for complete search history.

(56) References Cited

U.S. PATENT DOCUMENTS

| | | | |
|---|---|---|---|
| 8,377,483 B2* | 2/2013 | Makino | A01N 59/16 424/648 |
| 2003/0170315 A1* | 9/2003 | Makino | 424/648 |
| 2006/0088574 A1* | 4/2006 | Manning | A23L 1/296 424/439 |

FOREIGN PATENT DOCUMENTS

| | | |
|---|---|---|
| JP | 2-142760 | 5/1990 |
| JP | 2002-80376 | 3/2002 |
| WO | WO2010/073642 A1 | 7/2010 |
| WO | WO2012/063357 A1 | 5/2012 |

OTHER PUBLICATIONS

Nov. 12, 2010 International Search Report in connection with corresponding Application No. PCT/P2010/070184.

* cited by examiner

*Primary Examiner* — Michael B Pallay
(74) *Attorney, Agent, or Firm* — Dooper & Dunham LLP

(57) ABSTRACT

A bioactive agent in which the bioactive effectiveness of ferrous iron salt and/or ferric ferrous iron salt contained therein is stabilized, making long term preservation possible, so that the bioactive agent can be useful as an original solution for medical use, as a soil conditioner, or the like. An iron-magnesium mixture solution is provided in the invention, wherein the iron-magnesium mixture solution is produced by mixing an aqueous solution containing a ferrous iron salt and/or a ferric ferrous iron salt in a concentration of not less than 0.5 mol/L as iron in the ferrous iron salt and/or the ferric ferrous iron salt, and an aqueous solution containing a magnesium salt in a concentration of not less than 0.2 mol/L as magnesium in the magnesium salt.

18 Claims, 1 Drawing Sheet

METHOD FOR PRODUCING BIOACTIVE AGENT, BIOACTIVE AGENT PRODUCED THEREBY, COSMETIC, FRESHNESS-MAINTAINING AGENT, GROWTH PROMOTION AGENT, SOIL CONDITIONING AGENT, AND PHARMACEUTICAL STOCK SOLUTION

FIELD OF THE INVENTION

The present invention relates to a bioactive agent useful as a medicine, cosmetics, a freshness keeping agent, growth promoting agent for plants and animals, soil conditioner, and the like.

BACKGROUND OF THE INVENTION

For instance, an iron salt such as ferrous iron salt, and ferric ferrous iron salt, is bioactive and known to be useful as a medicine, cosmetics, a freshness keeping agent, growth promoting agent for plants and animals, and the like. For instance, water containing a ferric ferrous iron salt is well known as π-water.

PRIOR ART

Patent Document

Patent Document 1: Publication No. JP2002-80376

Outline Of The Invention

Nevertheless, there is a problem in that said iron salt is apt to be oxidized, and in a case where said iron salt is oxidized, the bioactive ability of said iron salt becomes unstable, so that the effect of said iron salt will deteriorates over a long term of preservation.

Means To Solve Said Problem

To solve said problem, hitherto a means to stabilize said iron salt with a magnesium salt has been provided (For instance, Patent Document 1).

The inventor of the present invention discovered that when said iron salt is stabilized by the magnesium salt, the stabilizing effectiveness of said magnesium salt for said iron salt becomes remarkable in a case where an aqueous solution which contains said iron salt in a concentration of not less than that which is prescribed, and an aqueous solution which contains said magnesium salt in a concentration of not less than that which is prescribed, are prepared separately, and then are mixed together. The present invention was thereby realized. Said bioactive agent has various uses, the optimum concentration range of said iron salt therein depending on its application.

Thereupon, in the present invention, said aqueous solution containing said iron salt in a concentration of not less than that which is prescribed, and said aqueous solution containing a magnesium salt in a concentration of not less than that which is prescribed are mixed together, to stabilize said iron salt by said magnesium salt, after which the resulting mixture solution is then diluted into the optimum concentration range determined for its application.

Thus, the present invention provides a method for producing a bioactive agent comprising; preparing an aqueous solution containing a ferrous iron salt, and/or a ferric ferrous iron salt in a concentration of not less than 0.5 mol/L as iron in said ferrous iron salt, and/or said ferric ferrous iron salt, and an aqueous solution containing a magnesium salt in a concentration of not less than 0.2 mol/L as magnesium in said magnesium salt; mixing the resulting aqueous solution of said ferrous iron and/or said ferric ferrous iron salt and the resulting aqueous solution of said magnesium salt; then diluting the resulting iron-magnesium mixture solution into a prescribed concentration.

It is desirable that the molar ratio of said ferrous iron salt, and/or said ferric ferrous iron salt in the resulting iron-magnesium mixture is set to be in the range of between 1:0.05 and 1:1.5 as an iron-magnesium molar ratio. Further, the present invention provides bioactive agent produced by the aforementioned method.

If desired, one or more kind(s) of vitamin(s) selected from a group consisting of vitamins C, E and K may be added to said bioactive agent in an amount in the range of between 1 and $10^6$ moles per 1 mole of iron in said ferrous iron salt, and/or said ferric ferrous iron salt.

In a case where said bioactive agent of the present invention is used as a cosmetic product, said cosmetic product is set to contain said bioactive agent in an amount in the range of between $5 \times 10^{-8}$ mol/L and $5.5 \times 10^{-6}$ mol/L as iron in said bioactive agent.

In a case where said bioactive agent of the present invention is used as a freshness keeping agent, said freshness keeping agent is set to contain said bioactive agent in an amount in the range of between $5 \times 10^{-8}$ mol/L and $5.5 \times 10^{-5}$ mol/L as iron in said bioactive agent.

In a case where said bioactive agent of the present invention is used as a growth promoting agent for plants and animals, said growth promoting agent is set to contain said bioactive agent in an amount in the range of between $5 \times 10^{-7}$ mol/L and $5.5 \times 10^{-5}$ mol/L as iron in said bioactive agent.

In the case where said bioactive agent of the present invention is used as a soil conditioner, said soil conditioner is set to contain said bioactive agent in an amount in the range of between $5 \times 10^{-7}$ mol/L and $5.5 \times 10^{-5}$ mol/L as iron in said bioactive agent.

In a case where said bioactive agent of the present invention is used as an original solution for medical use, said original solution is set to contain said bioactive agent in an amount in the range of between $2 \times 10^{-5}$ mol/L and $6 \times 10^{-3}$ mol/L as iron in said bioactive agent.

Said original solution is useful as an original solution for prophylactics or therapeutics for cancer, diabetes, hepatitis, collagen disease, or atopic dermatitis.

Effect Of The Invention

In the present invention, ferrous iron salt and/or ferric ferrous iron salt which are useful as bioactive agents is (are) stabilized by magnesium salt, and in a case where said iron salt is provided as an aqueous solution containing said iron salt in a concentration of not less than 0.5 mol/L as iron in said iron salt and said magnesium salt is provided as an aqueous solution containing said magnesium salt in a concentration of not less than 0.2 mol/L as magnesium in said magnesium salt, and both of said aqueous solutions are mixed together, it has been found that the stabilizing effect of the magnesium on iron remarkably improves. By applying the present invention, medicines, cosmetic products, freshness keeping agents, growth promoting agents, soil conditioners and the like which can be kept for a long time, can be provided.

PREFERRED EMBODIMENT TO EXECUTE THE PRESENT INVENTION

Figure 1:
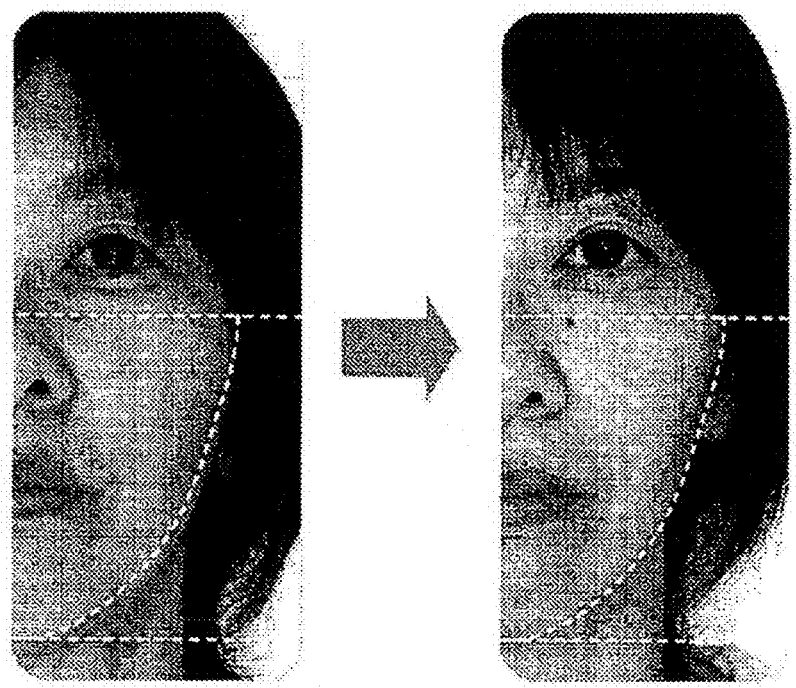
FIG. 1. A photograph illustrating the cosmetic effect, achieved by using fragrant lotion containing said bioactive agent of the present invention.

The present invention is explained precisely hereafter.

The iron salt in the present invention is water-soluble ferrous iron salt and/or ferric ferrous iron salt.

[Ferrous iron salt]

The ferrous iron salts, used as bioactive agent in the present invention, include inorganic acid salts of ferrous iron such as hydrochloride, sulfate nitrate, phosphate or the like, and organic acid salt of ferrous iron such as acetate, formate, oxalate, citrate, lactate, butyrate, succinate, propionate, or the like. Two or more kinds of ferrous iron salt may be used together.

[Ferric-Ferrous Iron Salt]

Ferric-ferrous iron salt of the present invention is iron salt having properties between ferrous iron salt and ferric iron salt, and said iron salt is such as inorganic acid salts (e.g. hydrochloride, sulfate, phosphate, nitrate and the like), organic acid salts (e.g. formate, acetate, oxalate, citrate, lactate, butyrate, succinate, propionate and the like). Said ferric-ferrous iron salt is prepared by putting ferric iron salt into a large quantity of strong alkaline aqueous solution such as sodium hydroxide, potassium hydroxide, lithium hydroxide, calcium hydroxide, or the like to cause valence conversion from ferric iron to ferrous iron, or putting ferrous iron salt into a large quantity of strong acid aqueous solution such as hydrochloride acid, sulfuric acid, or the like to cause valance conversion from ferrous iron to ferric iron, and said ferric-ferrous iron salt is obtained as transition form during said valence conversion. Concrete illustrations of methods of production of said ferric-ferrous iron salt are shown hereafter.

Commonly, two methods described below are applied to prepare said ferric-ferrous iron salt.

1. Method 1 (Preparation from Ferric Iron Salt)

Ferric chloride ($FeCl_3 \cdot 6H_2O$), 1.0 mg was dissolved in 100 ml of 0.5 N sodium hydroxide aqueous solution and stirred, then the solution was allowed to stand for overnight. After filtering out some insoluble products in the solution, the solution was neutralized with hydrochloric acid, then concentrated in a reduced pressure desiccator to get a dried and crystallized product. Thus the crystallized product with sodium chloride, that is, chloride of ferric-ferrous iron (hereinafter sometimes referred to as iron chloride [II, III]), was prepared. In the case of extracting iron chloride (II, III) from the crystallized product with sodium chloride, the product was dissolved in 50 ml of 80% by weight isopropyl alcohol aqueous solution to elute iron chloride (II, III). After separating the solution containing eluted iron chloride (II, III), the solution was concentrated at reduced pressure in order to remove the solvent and dry. Then the procedure consisting of elution, concentration and dry was repeated a few times. Thus iron chloride (II, III), 0.25 mg was extracted from the crystallized product with sodium chloride.

2. Method 2 (Preparation from Ferrous Iron Salt)

Ferrous sulfate ($FeSO_4 \cdot 7H_2O$), 1.0 mg was dissolved in 100 ml of 0.5 N HCl aqueous solution and stirred, then the solution was allowed to stand for overnight. After filtering out some insoluble products in the solution, the solution was concentrated in a reduced pressure desiccator to get a dried product. The dried product in powder was dissolved in 10 ml of 80% by weight isopropyl alcohol aqueous solution to elute iron chloride (II, III). After separating the solution containing eluted iron chloride (II, III), the solution was concentrated at reduced pressure in order to remove the solvent and dry. Then the procedure consisting of elution, concentration and dry was repeated a few times. Thus iron chloride (II, III), 0.6 mg was extracted for the crystallized product with sodium chloride.

[Magnesium Salt]

Magnesium salts, used in this invention are water soluble magnesium salts and include inorganic acid salts such as magnesium chloride, magnesium sulfate, magnesium phosphate, magnesium nitrate, or the like, and organic acid salts such as magnesium acetate, magnesium butyrate, magnesium formate, magnesium oxalate, magnesium citrate, magnesium propionate, or the like. Two or more kinds of magnesium salts may be used together.

[Preparation of the Bioactive Agent]

In the present invention, said ferrous iron salt and/or said ferric ferrous iron salt is (are) dissolved in water in a concentration of not less than 0.5 mol/L as iron in said iron salt, and not more than their solubility at room temperature, to prepare said iron aqueous solution.

Further, in the present invention, said magnesium salt is dissolved in water in a concentration of not less than 0.2 mol/L as magnesium in said magnesium salt, and not more than its solubility at room temperature, to prepare said magnesium aqueous solution.

Following this, the resulting iron aqueous solution and the resulting magnesium aqueous solution are mixed together. In a case where said iron aqueous solution has a not less concentration than is prescribed, and said magnesium aqueous solution also has a not less concentration than is prescribed, both of them being initially prepared separately, and then mixed together, it was found out that the stabilizing effect of said magnesium on said iron improved remarkably. The mixing ratio of said iron-magnesium is preferably set to be in the range of iron:magnesium=1:0.05 and 1:1.5 as a molar ratio.

As the water to be used to prepare the bioactive agent of the present invention, distilled water or deionized water are most preferable.

[Vitamins]

If desired, vitamins C, E, and/or K may be added to said bioactive agent of the present invention.

Two or more kinds of said vitamins may be added to said bioactive agent.

Said vitamin(s) may preferably be added in an amount in the range of between 1 and $10^6$ moles per 1 mole of said ferrous iron salt, and/or said ferric ferrous iron salt.

In a case where said vitamin(s) is (are) added, an increased strength and further stability in the bioactivation of said bioactive agent of the present invention will be realized.

[Third Component]

Vitamins besides vitamins C, E and K, hormones, fats and oils, lubricants, perfumes, sweeteners, or the like may also be added to said bioactive agent of the present invention.

Further, vitamins E and K are oil-soluble, while vitamin C is water-soluble, so that in a case where water-insoluble components such as said oil-soluble vitamins, fats and oils or the like(s) is (are) added to said bioactive agent of the present invention, the addition of a further surface active agent may be preferable. As said surface active agent, considering its influence on the human body, and the stability of the iron ion contained in said bioactive agent, or the like, a common surface active agent, such as is used in foods and/or cosmetics, is preferable. Said surface active agent may be a nonionic surface active agent such as a polyoxiethylene ester of fatty acid, sucrose ester of fatty acid, sorbitan ester of fatty acid, or the like.

[Use of Said Bioactive Agent]

In said bioactive agent, said iron salt is effectively stabilized by said magnesium salt, resulting in the long term maintenance of the preferable level of bioactivity. As aforementioned, when said bioactive agent is used, the iron-magnesium mixture solution, which is the bioactive agent, is diluted into a predetermined optimum concentration range according to the intended application.

For instance, in the case of a cosmetic product, said bioactive agent will be contained therein in a concentration in the range of between $5 \times 10^{-6}$ mol/L and $5.5 \times 10^{-4}$ mol/L as iron in said bioactive agent. In the case of a freshness keeping agent, said bioactive agent will be contained therein in a concentration in the range of between $5 \times 10^{-6}$ mol/L and $5.5 \times 10^{-4}$ mol/L as iron in said bioactive agent. In the case of the growth promoting agent for plants and animals, said bioactive agent will be contained therein in a concentration in the range of between $5 \times 10^{-6}$ mol/L and $5.5 \times 10^{-4}$ mol/L as iron in said bioactive agent. In the case of a soil conditioner, said bioactive agent will be contained therein in a concentration in the range of between $5 \times 10^{-6}$ mol/L and $5.5 \times 10^{-4}$ mol/L as iron in said bioactive agent. In the case of the medicine, said bioactive agent will be contained therein in a concentration in the range of between $2 \times 10^{-3}$ mol/L and $6 \times 10^{-3}$ mol/L as iron in said bioactive agent, to prepare an aqueous solution as an original solution, and said original solution will further be diluted with water into a prescribed degree of dilution according to the kind and severity of disease being treated, and then administered to a patient.

Said bioactive agent of the present invention is especially useful for the treatment and prevention of diseases such as cancer, diabetes, hepatitis, nephritis, renal insufficiency, ulcers of the stomach, duodenum, or the like, hypertension, collagen disease, allergic disease such as atopic dermatitis, hay fever etc., menstrual pain, and constipation, or the like, and further can be useful as an antibacterial agent which is harmless to man and beast.

EXAMPLE 1

Preparation of Ferrous-Ferric Iron Salt

Ferrous sulfate ($FeSO_4 \cdot 6H_2O$), 1 g was dissolved in 5 ml of 12 N HCl aqueous solution and stirred. Then the solution was filtered by filter paper (No. 5C) to remove some insoluble products. A portion of the filtered solution for sampling was concentrated in a reduced pressure desiccator to get a dried product. The dried product in powder was dissolved in 80% by weight isopropyl alcohol aqueous solution. Then the solution containing eluted component was concentrated at reduced pressure in order to remove the solvent and dry. In addition, the procedure consisting of elution, concentration and dry was repeated a few times. Thus crystallized product was prepared.

Five % by weight aqueous solution of said crystallized product was prepared, of which 0.01 ml was spotted on a point from 3 cm of the bottom of paper chromatography (PC) filter paper (2 cm×40 cm), then was developed by n-butyl alcohol:acetic acid:$H_2O$ (5:1:4, v/v/v) as developing solvent for 15 hours. After developing the filter paper was dried out, then colored by spray of 1% by weight potassium ferricyanide aqueous solution as coloring reagent. As a result, it was confirmed that the developed point of the crystallized product was one spot (Rf=0.07).

In addition, an equivalent mixture of $FeCl_2$ and $FeCl_3$ (1:1) was spotted on a paper chromatography (PC) filter paper as the same way. As a result, it was confirmed that there were two developed points ($FeCl_2$, Rf=0.095, $FeCl_3$, Rf=0.36) on the filter paper. These paper chromatography (PC) tests mentioned above accounted for the crystallized product as homogeneous product, not mixtures.

Further, a sample solution, 100 ml was prepared by means of dissolving 0.1 g of said crystallized product in distilled water. The sample solution (2.5 ml), 0.1% by weight ortho-phenanthroline aqueous solution (2.5 ml), and sodium acetate-acetic acid buffer solution, pH=4.5, (25 ml) were put into a mess-flask, then distilled water was put into said mess-flask up to its marked line. After being allowed to stand for 30 minutes at room temperature, an absorbance (510 nm) of the solution was measured. Ferrous iron in the sample solution was 0.019 g/100 ml calculated from standard curve, obtained by $FeCl_2$ solution in the same way.

Moreover, in the case of putting sample solution into the mess-flask, then hydroxylamine hydrochloride aqueous solution, 1.0 ml was added to the mess-flask beforehand in order to reduce ferric iron in the sample solution to ferrous iron. As a result, ferrous iron, 0.038 g/100 ml was gotten. It was confirmed that the crystallized product consisted of ferrous iron and ferric iron equivalently because of calculation of ferric iron, 0.019 g/100 ml (=0.038 g/100 ml−0.019 g/100 ml). From consideration of the above-mentioned test, it was concluded that the crystallized product would be $Fe_2Cl_5 \cdot xH_2O$.

EXAMPLE 2

Preparation of Ferrous-Ferric Iron Salt

Ferric chloride (1.0 mg) was dissolved in 5 ml of 10 N sodium hydroxide aqueous solution and stirred. After stirring, the solution was neutralized with 10 N hydrochloric acid, then was filtered by a filter paper (No. 5C) to remove some insoluble products. A portion of the filtered solution for sampling was concentrated in a reduced pressure desiccator to get a dried product. The dried product in powder was dissolved in 80% by weight isopropyl alcohol aqueous solution. Then the solution containing eluted component was concentrated at reduced pressure in order to remove the solvent and dry. In addition, the procedure consisting of elution, concentration and dry was repeated a few times. Thus the crystallized product was prepared. The crystallized product in this example was tested by the same way as Example 1 mentioned above. Thus, it was concluded that the crystallized product would be $Fe_2Cl_5 \cdot xH_2O$.

EXAMPLE 3

Identification Test for Safety

An aqueous solution of iron was prepared by dissolving $FeCl_2$ anhydride in distilled water so as to be at a concentration of 1 mol/L (not less than 0.5 mol/L) as iron in said $FeCl_2$ anhydride. An aqueous solution of magnesium was prepared by dissolving $MgCl_2$ anhydride in distilled water so as to be at a concentration of 0.5 mol/L (not less than 0.2 mol/L) as magnesium in said $MgCl_2$ anhydride.

(Sample 1)

Said aqueous solution of iron and said aqueous solution of magnesium were mixed together into a mass ratio of 1:2, and then the resulting mixture solution was diluted with distilled water to prepare Sample 1, containing $5 \times 10^{-3}$ mol/L of iron and $5 \times 10^{-3}$ mol/L of magnesium (molar ratio of iron to magnesium=1:1).

(Sample 2)

Said aqueous solution of iron and said aqueous solution of magnesium were mixed together into a mass ratio of 1:1.4, and then the resulting mixture solution was diluted with distilled water to prepare Sample 2, containing $5 \times 10^{-3}$ mol/L of iron and $3.5 \times 10^{-3}$ mol/L of magnesium (molar ratio of iron to magnesium=1:0.7).

(Sample 3)

Said aqueous solution of iron and said aqueous solution of magnesium were mixed together into a mass ratio of 1:1, and then the resulting mixture solution was diluted with distilled water to prepare Sample 3, containing $5 \times 10^{-3}$ mol/L of iron and $2.5 \times 10^{-3}$ mol/L of magnesium (molar ratio of iron to magnesium=1:0.5).

(Sample 4)

Said aqueous solution of iron and said aqueous solution of magnesium were mixed together into a mass ratio of 1:0.6, and then the resulting mixture solution was diluted with distilled water to prepare Sample 4, containing $5 \times 10^{-3}$ mol/L of iron and $1.5 \times 10^{-3}$ mol/L of magnesium (molar ratio of iron to magnesium=1:0.3).

(Sample 5)

Said aqueous solution of iron and said aqueous solution of magnesium were mixed together into a mass ratio of 1:0.2, and then the resulting mixture solution was diluted with distilled water to prepare Sample 5, containing $5 \times 10^{-3}$ mol/L of iron and $0.5 \times 10^{-3}$ mol/L of magnesium (molar ratio of iron to magnesium=1:0.1).

(Sample 6)

Said aqueous solution of iron and said aqueous solution of magnesium were mixed together into a mass ratio of 1:0.1, and then the resulting mixture solution was diluted with distilled water to prepare Sample 6, containing $5 \times 10^{-3}$ mol/L of iron and $0.25 \times 10^{-3}$ mol/L of magnesium (molar ratio of iron to magnesium=1:0.05).

(Comparison Sample 1)

$FeCl_2$ anhydride was dissolved in distilled water so as to be a concentration of 1 mol/L as iron in said $FeCl_2$ anhydride, and then the resulting aqueous solution of $FeCl_2$ anhydride was further diluted with distilled water to prepare Comparison sample 1 containing 0.0005 mol/L of iron (without magnesium).

(Comparison Sample 2)

An aqueous solution of iron was prepared by dissolving $FeCl_2$ anhydride in distilled water so as to be a concentration of 0.3 mol/L (less than 0.5 mol/L) as iron in said $FeCl_2$ anhydride. An aqueous solution of magnesium was prepared by dissolving $MgCl_2$ anhydride in distilled water so as to be a concentration of 0.1 mol/L (less than 0.2 mol/L) as magnesium in said $MgCl_2$ anhydride. The resulting aqueous solution of iron and the resulting aqueous solution of magnesium were mixed together into a mass ratio of 1:1, and then the resulting mixture solution was diluted with distilled water to prepare Comparison sample 2, containing $5 \times 10^{-3}$ mol/L of iron and $5 \times 10^{-3}$ mol/L of magnesium (molar ratio of iron to magnesium=1:0.5).

(Comparison Sample 3)

$FeCl_2$ anhydride and $MgCl_2$ anhydride were dissolved together at the same time in distilled water so as to be a concentration of $5 \times 10^{-3}$ mol/L as iron in said $FeCl_2$ anhydride, and a concentration of $2.5 \times 10^{-3}$ mol/L as magnesium in said $MgCl_2$ anhydride to prepare Comparison sample 3 (molar ratio of iron to magnesium=1:0.5).

Regarding said Samples 1 to 6 and said Comparison samples 1, 2 and 3 (n=3), an oxidation test was carried out under the conditions described as follows, after which the concentrations of $Fe^{2+}$ and $Fe^{3+}$ in each of the samples were measured separately by 1, 10-phenanthroline absorptiometry. The results are shown in Table 1.

Conditions of the Oxidation Test

The oxidation test was carried out by both air oxidation through aeration and compulsion oxidation using $H_2O_2$.

Aeration time: 150 hours

Aeration flow rate: 400 ml/min

After aeration, 0.3 mg/L of $H_2O_2$ was added.

TABLE 1

|  | Unit | Sample 1(Fe:Mg = 1:1 molar ratio) | | | Sample 2(Fe:Mg = 1:0.7 molar ratio) | | | Sample 3(Fe:Mg = 1:0.5 molar ratio) | | |
|---|---|---|---|---|---|---|---|---|---|---|
|  |  | n = 1 | n = 2 | n = 3 | n = 1 | n = 2 | n = 3 | n = 1 | n = 2 | n = 3 |
| Total Fe | mg/L | 30 | 30 | 30 | 30 | 30 | 30 | 30 | 30 | 30 |
| $Fe^{2+}$ |  | 24 | 25 | 25 | 27 | 27 | 26 | 29 | 29 | 29 |
| $Fe^{3+}$ |  | 6 | 5 | 5 | 3 | 3 | 4 | 1 | 1 | 1 |

|  | Unit | Sample 4(Fe:Mg = 1:0.3 molar raio) | | | Sample 5(Fe:Mg = 1:0.1 molar ratio) | | | Sample 6(Fe:Mg = 1:0.05 molar ratio) | | |
|---|---|---|---|---|---|---|---|---|---|---|
|  |  | n = 1 | n = 2 | n = 3 | n = 1 | n = 2 | n = 3 | n = 1 | n = 2 | n = 3 |
| Total Fe | mg/L | 30 | 30 | 30 | 30 | 30 | 30 | 30 | 30 | 30 |
| $Fe^{2+}$ |  | 28 | 28 | 28 | 27 | 28 | 27 | 25 | 26 | 25 |
| $Fe^{3+}$ |  | 2 | 2 | 2 | 3 | 2 | 3 | 5 | 4 | 5 |

|  | Unit | Comparison sample 1 (without Mg) | | | Comparison sample 2 (Fe solution is lower than 0.5 mole/L Mg solution is lower than 0.2 mole/L Fe:Mg = 1:0.5 molar ratio) | | | Comparison sample 3 (Fe, Mg dissolved simultaneous Fe:Mg = 1:0.5 molar ratio) | | |
|---|---|---|---|---|---|---|---|---|---|---|
|  |  | n = 1 | n = 2 | n = 3 | n = 1 | n = 2 | n = 3 | n = 1 | n = 2 | n = 3 |
| Total Fe | mg/L | 30 | 30 | 30 | 30 | 30 | 30 | 30 | 30 | 30 |
| $Fe^{2+}$ |  | 20 | 19 | 20 | 24 | 24 | 25 | 25 | 24 | 24 |
| $Fe^{3+}$ |  | 10 | 11 | 10 | 6 | 6 | 5 | 5 | 6 | 6 |

Referring to Table 1, Samples 1 to 6 in which $MgCl_2$ were each separately added in a molar ratio of iron to magnesium in the range of between 1:1 and 1:0.05, these samples showed good stabilizing effects of Mg in a molar ratio of iron to magnesium of 1:0.7 to 1:0.1, especially Sample 3 in which $MgCl_2$ was added in a molar ratio of iron to magnesium of 1:0.5, showing the remarkable stabilizing effect of Mg.

On the contrary, comparison sample 1 which did not contain Mg (without Mg) showed a larger amount of $Fe^{3+}$, as compared with Samples 1 to 6, so that it is recognized that in cases where there was no Mg contained, the $Fe^{2+}$ in said bioactive agent became unstable.

Further, comparing Sample 4 and Comparison sample 2, it is recognized that Comparison sample 2 which was prepared by mixing an aqueous solution of iron whose iron concentration was less than 0.5 mol/L and an aqueous solution of magnesium whose magnesium concentration was less than 0.2 mol/L had inferior stability of $Fe^{2+}$, as compared with Sample 3, which was prepared using aqueous solutions of iron and magnesium having concentration ranges of those in the present invention.

Further, comparing Sample 3 and Comparison Sample 3, Sample 3 was prepared by dissolving $FeCl_2$ and $MgCl_2$ separately in distilled water, and so it is recognized that Sample 3 had greater $Fe^{2+}$ stability than did Comparison sample 3 in which the iron and magnesium were dissolved in distilled water at the same time.

EXAMPLE 4

Preparation of Iron-Magnesium Mixture Solution 1

$FeCl_2$ anhydride was dissolved in distilled water in an amount so as to be a concentration of 0.6 mol/L as iron in said $FeCl_2$ anhydride to prepare an aqueous solution of iron.

$MgCl_2$ anhydride was dissolved in distilled water in an amount so as to be a concentration of 0.6 mol/L as magnesium in said $MgCl_2$ anhydride to prepare an aqueous solution of magnesium.

The resulting aqueous solution of iron and the resulting aqueous solution of magnesium were mixed together into a mass ratio of 1:1, and further, the resulting mixture solution was then diluted 100 times with distilled water to prepare an iron-magnesium mixture aqueous solution 1 (iron:magnesium 1:1 molar ratio).

EXAMPLE 5

Preparation of Iron-Magnesium Mixture Solution 2

$FeSO_4$ anhydride was dissolved in distilled water in an amount so as to be a concentration of 0.8 mol/L as iron in said $FeSO_4$ anhydride to prepare an aqueous solution of iron. $MgSO_4$ anhydride was dissolved in distilled water in an amount so as to be a concentration of 0.6 mol/L as magnesium in said $MgSO_4$ anhydride to prepare an aqueous solution of magnesium. The resulting aqueous solution of iron and the resulting aqueous solution of magnesium were then mixed together into a mass ratio of 1:1, and further diluted 100 times with distilled water to prepare an iron-magnesium mixture aqueous solution 2 (iron:magnesium, 1:0.5 molar ratio).

EXAMPLE 6

Preparation of Iron-Magnesium Mixture Solution 3

The ferric-ferrous iron salt prepared in EXAMPLE 1 was dissolved in distilled water so as to be a concentration of 1 mol/L as iron in said ferric-ferrous iron salt to prepare an aqueous solution of iron.

$MgCl_2$ anhydride was dissolved in distilled water in an amount so as to be a concentration of 1 mol/L as magnesium in said $MgCl_2$ anhydride.

The resulting aqueous solution of iron and the resulting aqueous solution of magnesium were then mixed together into a mass ratio of 1:1, and further diluted 100 times with distilled water to prepare an iron-magnesium mixture aqueous solution 3 (iron:magnesium, 1:0.5 molar ratio).

EXAMPLE 7

Preparation of Iron-Magnesium Mixture Solution 4

The ferric-ferrous iron salt prepared in EXAMPLE 2 was dissolved in distilled water so as to be a concentration of 1 mol/L as iron in said ferric-ferrous iron salt to prepare an aqueous solution of iron.

$MgSO_4$ anhydride was then dissolved in distilled water in an amount so as to be a concentration of 0.3 mol/L as magnesium in said $MgSO_4$ anhydride.

The resulting aqueous solution of iron and the resulting aqueous solution of magnesium were mixed together into a mass ratio of 1:1, and further diluted 100 times with distilled water to prepare iron-magnesium mixture aqueous solution 4 (iron:magnesium, 1:0.3 molar ratio).

EXAMPLE 8

Preparation of Iron-Magnesium Mixture Aqueous Solution Containing Vitamin C

Vitamin C was added to said iron-magnesium mixture aqueous solution 1 prepared in EXAMPLE 4 in an amount so as to be 100 moles of vitamin C per 1 mole of iron in said iron-magnesium mixture aqueous solution 1 to prepare an iron-magnesium mixture aqueous solution 5 containing vitamin C (iron:magnesium:vitamin C=1:1:100 molar ratio).

EXAMPLE 9

Preparation of Iron-Magnesium Mixture Aqueous Solution Containing Vitamin E

Vitamin E was added to said iron-magnesium mixture aqueous solution 2 prepared in EXAMPLE 5 in an amount so as to be 1 mole of vitamin E per 1 mole of iron in said iron-magnesium mixture aqueous solution 2, and further, polyethylene glycol mono stearate as a surface-active agent was added to said aqueous solution 2 in an amount so as to be 0.5% by mass to said mixture aqueous solution 2, to prepare an iron-magnesium mixture aqueous solution 6 containing vitamin E (iron:magnesium:vitamin E=1:0.5:1 molar ratio).

EXAMPLE 10

Preparation of Iron-Magnesium Mixture Aqueous Solution 7 Containing Vitamin K

Vitamin K was added to said iron-magnesium mixture aqueous solution 3 prepared in EXAMPLE 6 in an amount so as to be 3 moles of vitamin K per 1 mole of iron in said iron-magnesium mixture aqueous solution 3, and further myristic acid cane sugar ester as a surface active agent was added to said mixture aqueous solution 3 in an amount so as to be 0.5% by mass to said mixture aqueous solution 3, to prepare an iron-magnesium mixture aqueous solution 7 containing vitamin K (iron:magnesium:vitamin K=1:0.5:3 molar ratio).

[Comparison 1] (Preparation of Iron Aqueous Solution 1 without Magnesium for Comparison)

$FeCl_2$ anhydride was dissolved in distilled water in an amount so as to be a concentration of 0.6 mol/L as iron in said $FeCl_2$ anhydride, and further the resulting aqueous solution was then diluted 100 times with distilled water, to prepare an iron aqueous solution without magnesium for comparison.

[Comparison 2] (Preparation of Iron-Magnesium Mixture Aqueous Solution 2 without Magnesium for Comparison)

$FeCl_2$ anhydride was dissolved in distilled water in an amount so as to be a concentration of 0.3 mol/L (less than 0.5 mol/L) as iron in said $FeCl_2$ anhydride, to prepare an aqueous solution of iron. $MgCl_2$ anhydride was then dissolved in distilled water in an amount so as to be a concentration of 0.1 mol/L (less than 0.2 mol/L) as magnesium in said $MgCl_2$ anhydride, to prepare an aqueous solution of magnesium.

The resulting aqueous solution of iron and the resulting aqueous solution of magnesium were then mixed together into a mass ratio of 1:3, and further, the resulting mixture aqueous solution was then diluted 25 times with distilled water, to prepare an iron-magnesium mixture aqueous solution 2 (iron:magnesium=1:1 molar ratio) for comparison.

[Comparison 3] (Preparation of Iron-Magnesium Mixture Aqueous Solution 3 for Comparison)

$FeSO_4$ anhydride and $MgSO_4$ anhydride were dissolved together at the same time in distilled water so as to be a concentration of $FeSO_4$ anhydride with 0.8 mol/L as iron in said $FeSO_4$ anhydride and a concentration of $MgSO_4$ anhydride with 0.4 mol/L as magnesium in said $MgSO_4$ anhydride, and further the resulting mixture aqueous solution was then diluted 100 times with distilled water, to prepare an iron-magnesium mixture aqueous solution 3 (iron:magnesium=1:0.5 molar ratio) for comparison.

EXAMPLE 11

Freshness Maintenance Test 1

Said iron-magnesium mixture aqueous solution 1 was kept for one year at room temperature, after which said mixture aqueous solution was diluted 10000 times with distilled water, to prepare a freshness maintaining solution. Said freshness maintaining solution contained $1.3 \times 10^{-7}$ mol/L of iron and $3 \times 10^{-7}$ mol/L of magnesium.

Ten pieces of flat fish were dipped in said freshness maintaining solution, after which said pieces of flat fish were each strained with filter paper. Following this, said strained pieces of flat fish were wrapped in polyvinylidene chloride film to preserve them at 10° C. The average K value of said 10 pieces of flat fish after having been preserved for 10 days, was 15%, and said pieces of flat fish could satisfactorily be served to be eaten raw.

Further, said freshness maintaining solution was kept for two years at room temperature, following which the same test as described above was carried out. The results showed the average K value of the 10 pieces of flat fish preserved to be 30%, and said flat fish pieces could satisfactorily be served and eaten after heating.

Estimations of K values for fish are described as follows.

| | |
|---|---|
| Live fish, pieces of raw fish rinsed in cold water | not more than 15% |
| Sashimi | not more than 20% |
| General fresh fish | not more than 35% |
| Raw material for processing | not more than 60% |
| Beginning of decomposition | not less than 60% |

EXAMPLE 12

Freshness Maintenance Test 2

Using said iron-magnesium mixture aqueous solution 5 containing vitamin C of EXAMPLE 8 instead of said iron-magnesium mixture solution 1 of EXAMPLE 11, a freshness maintaining solution 2 was prepared in the same way as in EXAMPLE 11, and the same freshness maintenance test as in EXAMPLE 11 was carried out for said freshness maintaining solution 2.

The average K value of 10 pieces of the flat fish after 10 days preservation was 12%, and after two years preservation of said freshness maintaining solution 2, the test results showed that the average K value of said 10 pieces of flat fish was 25%.

[Comparison 4] (Comparison Freshness Maintenance Test 1)

Said iron aqueous solution 1 without magnesium for comparison prepared in COMPARISON 1, was kept for one year at room temperature, following which said solution was then diluted 10000 times with distilled water to prepare Comparison freshness maintaining solution 1. Ten pieces of flat fish were dipped in said Comparison freshness maintaining solution 1 the same as in EXAMPLE 8, after which said pieces of flat fish were then each strained with filter paper. Following this, said strained pieces of flat fish were then wrapped in polyvinylidene chloride film and preserved at 10° C. The average K value of said 10 pieces of flat fish after 10 days preservation was 50%, and said flat fish pieces could be barely used for food, and it is recognized that the freshness maintaining ability of said Comparison freshness maintaining solution 1 was lower than those of said freshness maintaining solutions 1 and 2 of the present invention.

Following this, said iron aqueous solution 1 without magnesium for Comparison was kept for two years at room temperature, following which the same test as described above was carried out. The test result showed that the average K value of said 10 pieces of flat fish was 60%, and that said pieces of flat fish were within the limits of condition to be used for food.

[Comparison 5] (Comparison Freshness Maintenance Test 2)

Using said Comparison iron-magnesium mixture aqueous solution 2 of COMPARISON 2 (iron 0.3 mol/L [<0.5 mol/L] of said iron aqueous solution in a separate state, magnesium 0.1 mol/L [<0.2 mol/L] of said magnesium aqueous solution in a separate state, iron:magnesium=1:1 molar ratio in the mixed aqueous solution), instead of the iron-magnesium mixture solution 1 of Example 11, a Comparison freshness maintaining solution 2 was prepared in the same way as in EXAMPLE 11, and the same freshness maintenance test as in EXAMPLE 11 was carried out.

The resulting K value after 10 days preservation was 42%, and said flat fish pieces were not in a suitable condition to be eaten raw, and it is recognized that the freshness maintaining ability of said Comparison freshness maintaining solution 2 was lower than the freshness maintaining abilities of said freshness maintaining solutions 1 and 2 of the present invention, the same as the Comparison freshness maintaining solution 1.

Further, said comparison freshness maintaining solution 2 was kept for two years, after which the same test was carried out, the result being that the average K value of the 10 pieces of flat fish was 58%, this value showing that, the condition of said pieces indicated that they were barely usable as processed raw material.

[Comparison 6] (Comparison Freshness Maintenance Test)

Instead of said iron-magnesium mixture aqueous solution 1 of Example 11, using said Comparison iron-magnesium mixture aqueous solution 3 of COMPARISON 3 (iron and magnesium are dissolved in distilled water at the same time, wherein the concentrations of iron and magnesium were each set to be 0.8 mol/L iron and 0.4 mol/L magnesium), a Comparison freshness maintaining solution 3 was prepared in the same way as in EXAMPLE 11, and the freshness maintenance test the same as the test in EXAMPLE 11 was carried out. As a result, the K-value after 10 days of preservation was 42% and the pieces of the flat fish were in an unsuitable condition to be eaten eating raw, so it is recognized that said Comparison freshness maintaining solution 3 has a lower freshness maintenance ability than said freshness maintaining solutions 1, 2 of the present invention, the same as said comparison freshness maintaining solutions 1, 2.

Further, said Comparison freshness maintaining solution 2 was kept for two years at room temperature, after which the same test was carried out. As a result, the average K-value of the 10 pieces of flat fish was 56%, this value showing that the condition of said pieces indicated that they were barely usable as a processed raw material.

[Comparison 7]

As COMPARISON 7, the same preservation test using pieces of flat fish which were dipped in distilled water was carried out. The resulting K value of said pieces of flat fish after 10 days preservation was about 70%, making said pieces of flat fish unsuitable for food use.

Considering the results of EXAMPLES 11 and 12 and COMPARISONS 4 to 7, it is recognized that according to the preparation method of the present invention, iron has a sufficient freshness maintaining effect with the addition of magnesium, even when the freshness maintaining agent containing both iron and magnesium is kept for more than one year.

EXAMPLE 13

Said iron-magnesium mixture aqueous solution 2, prepared one year ago, was diluted 1000 times with distilled water, to prepare a growth promoting agent 1 for plants. Using said test agent 1, pumpkins, potatoes and onions are each cultivated. The conditions of said harvested vegetables are described below.

[Pumpkins]
Appearance: The pumpkins have glossy appearances, and in particular have a thick bright orange colored pulp, and contain twice or more the amount of carotene as compared with ordinary ones.

Taste: Soft and crumbly and sweet. Said pumpkin has a very high sugar content of 10.6 degrees (generally 7 degrees).

[Potatoes]
Appearance: The potatoes have white skins, and in particular have fewer shoots on their surface.
Starch: 18.8% (generally 16%)
Vitamin C: 32 mg/100 g (generally 23 mg/100 g)
Taste: Perfect, being soft and fluffy, and easily crushed in the mouth, and having the special smell and body of potato. Further, said potatoes are suitable for salad use, since said potatoes have little harshness.

[Onions]
Appearance: Having a glossy appearance and uniform size. Their skin can be easily peeled and pulp is tight and firm. Being storable for a long time. It was recognized by an electron microscope or the like that said onion was a healthy crop having tissue in which small cells were packed closely.

Taste: Being easily cut by a kitchen knife, said onion has good taste for eating raw. Since the sugar content degree of said onion is 10 degree, much higher than the ordinary (6 degree) and said onion has pleasant crispiness feeling on biting, said onion is suitable for salad and the like and does not crumble by stir frying.

EXAMPLE 14

Said iron-magnesium mixture aqueous solution 6 containing vitamin E in EXAMPLE 9, prepared 1.5 years ago, was diluted 1000 times with distilled water, to prepare a growth promoting agent 2 for plants. Using said growth promoting agent 2, pumpkin, potato and onion are each cultivated. Conditions of said harvested vegetables are described below.

[Pumpkins]
Appearance: The pumpkins have glossy appearances, and in particular have a thick bright orange colored pulp, and contain twice or more the amount of carotene as compared with ordinary ones.

Taste: Soft and crumbly and sweet. Said pumpkin has a very high sugar content of 10.9 degrees (generally 7 degrees).

[Potatoes]
Appearance: The potatoes have white skins, and in particular have fewer shoots on their surface.
Starch: 18.8% (generally 16%)
Vitamin C: 32 mg/100 g (generally 23 mg/100 g)
Taste: Perfect, being soft and fluffy, and easily crushed in the mouth, and having the special smell and body of potato. Further, said potatoes are suitable for salad use, since said potatoes have little harshness.

[Onions]
Appearance: Having a glossy appearance and uniform size. Their skin can be easily peeled and pulp is tight and firm. Being storable for a long time. It was recognized by an electron microscope or the like that said onion was a healthy crop having tissue in which small cells were packed closely.

Taste: Being easily cut by a kitchen knife, said onion has good taste for eating raw. Since the sugar content degree of said onion is 11 degree, much higher than the ordinary (6 degree) and said onion has pleasant crispiness feeling on biting, said onion is suitable for salad and the like and does not crumble by stir frying.

EXAMPLE 15

Medical Efficacy

Said iron-magnesium mixture aqueous solution 3, prepared in EXAMPLE 6 was kept for one year at room temperature, after which it was used in order to evaluate its medical efficacy. In a case where said mixture aqueous solution 3 is to be used as a medicine, said mixture aqueous solution 3 is to be diluted 100 times with distilled water, to prepare an original solution, and the following drinking method is applied.

(1) The following quantity of the original solution of said original solution is added to a cup of water (in an amount of about 150 ml), mixed well and then said diluted solution is to be drunk three times a day, when getting up, before lunch, and prior to going to bed.

(2) Drinking quantity after drinking start
   First week: 3 drops×3 times a day (9 drops in a day)
   Second week: 5 drops×3 times a day (15 drops in a day)
   Third week: 10 drops×3 times a day (30 drops in a day)
   Fourth week: 20 drops×3 times a day (60 drops in a day)

(3) Drinking quantity after fifth week
   a. Cancer: 30 drops×3 times a day (90 drops in a day)
   b. Diabetes, Hepatitis, Gastric ulcer, Heart disease, Asthma, Hypertension, etc.: 20 drops×3 times a day (60 drops in a day)
   c. Renal insufficiency, Rheumatism, Atopic dermatitis, Pollinosis, etc.: 10 drops×3 times a day (30 drops in a day)
   d. Dysmenorrhea, Obstipation, Sickness from drinking, other minor diseases: 10 drops×once a day (10 drops in a day)
   e. Maintenance of health: 3 drops×3 times a day (9 drops in a day)

The results in a case where said solution was administered to patients having various diseases, according to the aforementioned drinking methods, are shown in Tables 2 to 12.

(In any of said Tables, the numerical values of the test data in the upper rows show the pre-administration numerical values, while the numerical values of the test data in the lower rows show the post-administration numerical values.)

TABLE 2

| | | patients | | | inspection data | | | |
|---|---|---|---|---|---|---|---|---|
| cases | name of disease | sex | age | blood sugar level *1 | HbA1c *2 | neutral fat *3 | observation | |
| 1 | diabetes | male | 67 | 328 | 9.4 | 346 | Numerical values were improved after drinking for three months, as shown in Table. | |
| | | | | 183 | 7.4 | 210 | | |
| 2 | diabetes | female | 65 | 372 | 10.5 | 257 | Numerical values were improved after drinking for three months, as shown in Table. | |
| | | | | 270 | 8.9 | 130 | | |
| 3 | diabetes | male | 45 | 526 | 13 | 381 | At the start of drinking, having been taking 20 units of insulin, and 2 tablets of the blood sugar descending agent, one tablet before breakfast, and one tablet before supper, but stopped taking them after drinking for three months. | |
| | | | | 104 | 5.4 | 128 | | |
| 4 | diabetes | female | 57 | 325 | 9.5 | 231 | Numerical values were improved after drinking for three months, as shown in Table. | |
| | | | | 142 | 6.2 | 120 | | |

*1 the blood sugar level: normal values 70-110 ml/dl
*2 HbA1c: normal values 4.0-6.0%
*3 neutral fat (triglyceride): normal values 50-140 mg/dl

TABLE 3

| | name of | patients | | inspection data | |
|---|---|---|---|---|---|
| cases | disease | sex | age | blood pressure *1 | observation |
| 1 | high blood pressure | female | 53 | 194/118 | Numerical values stabilized after drinking for one month. |
| | | | | 148/69 | |
| 2 | high blood pressure and cerebrovascular infarction | female | 48 | 137/99 | Blood pressure had barely been kept at 135/96 as a result of taking the blood pressure descending agents, but after drinking for three months, could stop taking, and after drinking for five months, numerical values were improved, as shown in Table. |
| | | | | 119/83 | |
| 3 | diabetes | male | 65 | 185/126 | Subjective symptoms vanished completely after drinking for three months, and numerical values were improved, as shown in Table. |
| | | | | 138/85 | |

*1 blood pressure: normal values 139-101/89-61 mmHg

TABLE 4

| | | patient | | inspection data | | | | | | |
|---|---|---|---|---|---|---|---|---|---|---|
| case | name of disease | sex | age | RBC *1 | WBC *2 | Hb *3 | Ht *4 | BUN *5 | CRP *6 | observation |
| 1 | systemic lupus erythematosus | female | 35 | 3.3 million | 9200 | 7.6 | 23.7 | 34 | 5 | Normal numerical values were improved after drinking for 12 months, as shown in Table. |
| | | | | 4.2 million | 6500 | 12.2 | 37.3 | 17.1 | 0.5 | |

*1 RBC = erythrocyte (red) count(red blood corpuscles): normal values 3.5 million-4.5 million/mm$^3$
*2 WBC = leukocyte (white) count: normal values 4000-9000/mm$^3$
*3 Hb = hemoglobin: normal values 2-15 g/dl
*4 Ht = hematocrit: normal values 36-45% (adult female)
*5 BUN = blood urea nitrogen: normal values 8~20 mg/dl
*6 CRP: normal values less than 1.0 mg/dl

TABLE 5

| cases | name of disease | patients sex | age | GOT *1 | GPT *2 | γ-GTP *3 | tumor marker AFP *4 | tumor marker TPA *5 | observation |
|---|---|---|---|---|---|---|---|---|---|
| 1 | cancer of the liver | male | 63 | 60 / 45 | 65 / 28 | 191.3 / 78.8 | 48.4 / 18.3 | 291 / 97 | Since he was diagnosed with liver cancer three years ago, he had been treated with an anticancer drug. Numerical values were improved after drinking for three months, as shown in Table. |
| 2 | cancer of the liver | male | 57 | 129 / 57 | 78 / 40 | 215.1 / 88.7 | 55.6 / 18.5 | 318 / 97 | Progressing form viral hepatitis type C → Cirrhosis →liver cancer, but the condition was improved and his numerically valued tumor marker also showed improvement after drinking for six months, as shown in Table. |

*1 GOT: normal values 5-35 KU/ml
*2 GPT: normal values 5~25 KU/ml
*3 γ-GTP: normal values less than 40 units (adult)
*4 tumor marker AFP: normal values less than 20 ng/ml (RIA)
*5 tumor marker TPA: normal values less than 110 U/l (RIA)

TABLE 6

| cases | name of disease | patients sex | age | tumor marker PAP *1 | tumor marker PSA *2 | CA125 *3 | CA19-9 *4 | observation |
|---|---|---|---|---|---|---|---|---|
| 1 | cancer of the prostate | female | 48 | 220 / 0.6 | | | | Numerical values were improved by drinking for three months, as shown in Table. |
| 2 | cancer of the prostate | male | 62 | | 4.3 / 1.5 | | | Complete recovery by drinking for two months. |
| 3 | ovarian cancer | female | 60 | | | 283 / 34 | | A tumor having a size of about 5 cm had reduced to about 1 cm after drinking for six months, and numerical values were improved after one year, as shown in Table. |
| 4 | cancer of the colon | female | 36 | | | | 44.9 / 34.2 | Numerical values were improved by drinking for three months, as shown in Table. |

*1 tumor marker PAP: normal values less than 3.0 ng/ml (RIA)
*2 tumor marker PSA: normal values less than 3.0 ng/ml (RIA)
*3 CA125: normal values less than 50 U/ml
*4 CA19-9: normal values less than 37 U/ml

TABLE 7

| cases | name of disease | patients sex | age | WBC *1 | white blood corpuscles *2 | blood platelets *3 | protein M *4 | CA125 *5 | CA19-9 *6 | observation |
|---|---|---|---|---|---|---|---|---|---|---|
| 1 | acute myelocytic leukemia | female | 50 | 1900 / 3900 | | | | | | Headache, stiff shoulders, nausea, back muscleache, constipation, halitosis and the like wholly vanished, and physical condition was also improved after drinking for three months. |
| 2 | myelocytic leukemia | male | 65 | | 9500 / 5700 | 62000 / 188000 | | | | Numerical values were improved after drinking for 10 days, as shown in Table. |
| 3 | multiple myeloma | female | 65 | | 2500 / 3400 | 75000 / 118000 | 9100 / 2190 | | | Numerical values of leukocyte and thrombocyte were improved to reach certainly normal numerical values, although the present numerical values were still rather lower, after drinking for three months, than normal numerical values. |
| 4 | hypoplastic anemia | female | 38 | | | | | 2200 / 38 | 980 / 76 | First, by inspection, it was doubtful that this anemia was malignant, but numerical values were improved after drinking for three months, as |

TABLE 7-continued

| | | patients | | | inspection data | | | | | |
| --- | --- | --- | --- | --- | --- | --- | --- | --- | --- | --- |
| cases | name of disease | sex | age | WBC *1 | white blood corpuscles *2 | blood platelets *3 | protein M *4 | CA125 *5 | CA19-9 *6 | observation |
| | | | | | | | | | | shown in Table, confirming that this anemia was benign. |

*1 WBC: normal values 4000-9000/mm³
*2 white blood corpuscles: normal values 4000-9000/mm³
*3 blood platelets: normal values 0.2-0.4 million/mm³
*4 protein M: normal values less than 1700/mm³
*5 CA125: normal values less than 50 U/ml
*6 CA19-9: normal values less than 37 U/ml

TABLE 8

| | | patients | | inspection data | | | | |
| --- | --- | --- | --- | --- | --- | --- | --- | --- |
| cases | name of disease | sex | age | GOT *1 | GPT *2 | γ-GTP *3 | ZTT *4 | observation |
| 1 | hepatitis | female | 61 | 82 | 107 | | | Two kinds of herbal medicine were taken to no effect, but |
| | | | | 34 | 37 | | | improvement was noted after drinking for one month. |
| 2 | chronic viral hepatitis type B | male | 50 | 80 | 138 | | | Numerical values were completely improved after drinking for |
| | | | | 30 | 18 | | | three months. |
| 3 | viral hepatitis type B | male | 45 | 89 | 43 | | | Numerical values were completely improved after drinking for one |
| | | | | 30 | 15 | | | month. |
| 4 | viral hepatitis type C | female | 49 | 94 | 167 | 96 | 17 | Liver functions began to improve by drinking for one month. |
| | | | | 41 | 84 | 60 | 10.4 | |
| 5 | chronic viral hepatitis type C | male | 65 | 93 | 185 | | | Quantitative-qualitative analysis reaction of the antigen of virus |
| | | | | 18 | 16 | | | type C hepatitis became negative by drinking for one year. |

*1 GOT: normal values 5-35 KU/ml
*2 GPT: normal values 5-25 KU/ml
*3 γ-GTP: normal values less than 40 units (adult)
*4 ZZT: normal values 2-14 units

TABLE 9

| | | patients | | inspection data | | |
| --- | --- | --- | --- | --- | --- | --- |
| cases | name of disease | sex | age | CRP *1 | RF *2 | observation |
| 1 | multiple articular rheumatism | female | 66 | 1.9 | 115 | Numerical values were improved by drinking for three |
| | | | | 0.5 | 46 | months, as shown in Table. |
| 2 | rheumatism | male | 51 | 2.2 | 82 | Numerical values were improved with swelling and aching |
| | | | | 0.9 | 35 | of fingers also showing improvement after drinking for three months, as shown in Table. |

*1 CRP: normal values less than 1.0 mg/dl
*2 RF = rheumatoid factors: normal values less than 35 U/ml

TABLE 10

| | | patients | | inspection data | | | | | |
| --- | --- | --- | --- | --- | --- | --- | --- | --- | --- |
| cases | name of disease | sex | age | Ige-RIST *1 | cat *2 | cedar *3 | house dust *4 | weeds *5 | observation |
| 1 | atopic dermatitis | male | 42 | 4158 | 11.65 | 40.27 | ≥100 | 3.26 | Numerical values were improved after drinking for four |
| | | | | 720 | 8.3 | 30.2 | 58 | 2.0 | months, as shown in Table, while at the same time, the taking of steroid medication became unnecessary. |
| 2 | atopic dermatitis | male | 25 | 1674 | | | | | Conditions seemed more improved than the improved |
| | | | | 1268 | | | | | numericla values indicated, by drinking for five months. |

*1 Ige-RIST: normal values less than 280 IU/ml
*2 cat: normal values less than 0.34 UA/ml
*3 cedar: normal values less than 0.34 UA/ml
*4 house dust: normal values less than 0.34 UA/ml
*5 weeds: normal values less than 0.34 UA/ml

TABLE 11

| case | name of disease | patient sex | age | inspection data MRSA*1 | observation |
|---|---|---|---|---|---|
| 1 | MRSA | female | 76 | positive negative | Methicillin-Resistant *Staphylococcus Aureus* (MRSA) positive changed to MRSA negative by drinking for three months. |

*1MRSA: normal values negative

TABLE 12

| cases | name of disease | patients sex | age | inspection data tri-glyceride*1 | obesity index*2 | γ-GTP *3 | amount of urine*4 | observation |
|---|---|---|---|---|---|---|---|---|
| 1 | obesity | female | 60 | 236<br>164 | +17.4%<br>+9.2% | | | Numerical values were improved by drinking for three months, as shown in Table. |
| 2 | emaciation and slight hepatopathy | female | 46 | | −16.7%<br>−7.0% | 88<br>42 | | Numerical values were improved by drinking for three months, as shown in Table. |
| 3 | chronic renal failure | male | 43 | | | | 40-90<br>480 | Quantity of urine was reduced to numerical value after drinking for three months, as shown in Table. |

*1triglyceride: normal values 50-140 mg/dl
*2obesity index: normal values −10-+10%
*3 γ-GTP: normal values less than 40 units (Adult)
*4amount of urine: normal values 500-2000 ml/day

EXAMPLE 16

Medical Efficacy

Said iron-magnesium mixture aqueous solution 7 containing vitamin K prepared in EXAMPLE 10 was kept for one year at room temperature, and then used in order to evaluate the medical efficacy.

In a case where said mixture aqueous solution 7 containing vitamin K is used as a medicine, it is to be diluted 100 times with distilled water, to prepare the original solution, and generally the following drinking method is applied.
(1) The following quantity of the original solution of said original solution is added to a cup of water (in an amount of about 150 ml), mixed well and then said diluted solution is to be drunk three times a day, when getting up, before lunch, and prior to going to bed.
(2) Drinking quantity after drinking start
  First week: 3 drops×3 times a day (9 drops in a day)
  Second week: 5 drops×3 times a day (15 drops in a day)
  Third week: 10 drops×3 times a day (30 drops in a day)
  Fourth week: 20 drops×3 times a day (60 drops in a day)
(3) Drinking quantity after fifth week
  (a) Cancer: 30 drops×3 times a day (90 drops in a day)
  (b) Diabetes, Hepatitis, Gastric ulcer, Heart disease, Asthma, Hypertension, etc.: 20 drops×3 times a day (60 drops in a day)
  (c) Renal insufficiency, Rheumatism, Atopic dermatitis, Pollinosis, etc.: 10 drops×3 times a day (30 drops in a day)
  (d) Dysmenorrhea, Obstipation, Sickness from drinking, other minor diseases: 10 drops×once a day (10 drops in a day)
  (e) Maintenance of health: 3 drops×3 times a day (9 drops in a day)

The results in a case where said solution was administered to patients having various diseases, according to the aforementioned drinking methods, are shown in Tables 13 to 15.

TABLE 13

| cases | name of disease | patients sex | age | inspection data blood sugar level *1 | HbAlc *2 | neutral fat *3 | observation |
|---|---|---|---|---|---|---|---|
| 1 | diabetes | male | 58 | 352<br>174 | 10.4<br>7.2 | 361<br>245 | Numerical values were improved after drinking for three months, as shown in Table. |
| 2 | diabetes | female | 62 | 340<br>162 | 9.8<br>7.0 | 284<br>156 | Numerical values were improved after drinking for three months, as shown in Table. |

*1 the blood sugar level: normal values 70-110 ml/dl
*2 HbAlc: normal values 4.0-6.0%
*3 neutral fat (triglyceride): normal values 50-140 mg/dl

TABLE 14

| name of cases | disease | patients sex | age | inspection data GOT *1 | GPT *2 | γ-GTP *3 | tumor marker AFP *4 | tumor marker TPA *5 | observation |
|---|---|---|---|---|---|---|---|---|---|
| 1 | cancer of the liver | male | 58 | 62 42 | 67 23 | 194.5 75.4 | 49.2 18.2 | 315 94 | Since he was diagnosed with liver cancer three years ago, he had been treated with an anticancer drug. Numerical values were improved after drinking for three months, as shown in Table. |
| 2 | cancer of the liver | female | 67 | 114 54 | 72 41 | 211.6 85.3 | 56.1 18.3 | 307 92 | Progressing form viral hepatitis type C → Cirrhosis →liver cancer, but the condition was improved and his numerically valued tumor marker also showed improvement after drinking for six months, as shown in Table. |

*1 GOT: normal values 5-35 KU/ml
*2 GPT: normal values 5~25 KU/ml
*3 γ-GTP: normal values less than 40 units (adult)
*4 tumor marker AFP: normal values less than 20 ng/ml (RIA)
*5 tumor marker TPA: normal values less than 110 U/l (RIA)

TABLE 15

| name of cases | disease | patients sex | age | inspection data blood pressure *1 | observation |
|---|---|---|---|---|---|
| 1 | high blood pressure | male | 74 | 185/106 134/66 | Numerical values stabilized after drinking for two months. |

*1 blood pressure: normal values 139-101/89-61 mmHg

EXAMPLE 17

1. Preparation of a Soil Conditioner

The aqueous solutions described as follows were kept for one year at room temperature after preparation, after which said aqueous solutions were each diluted 1000 times with distilled water, to prepare soil conditioner samples described as follows.

Soil conditioner 1: a 1000 times diluted solution of said iron-magnesium mixture aqueous solution 4 (iron:magnesium=1:0.3 molar ratio) prepared in EXAMPLE 7.

Soil conditioner 2: a 1000 times diluted solution of said iron-magnesium mixture aqueous solution 7 containing vitamin K (iron:magnesium vitamin K=1:0.5:5 molar ratio) prepared in EXAMPLE 10.

Comparison soil conditioner 1: a 1000 times diluted solution of said iron aqueous solution without magnesium prepared in COMPARISON 1.

Comparison soil conditioner 2: a 1000 times diluted solution of said iron-magnesium mixture aqueous solution 2 prepared in COMPARISON 2 (a single iron aqueous solution, iron:0.3 mol/L [<0.5 mol/L], a single magnesium aqueous solution, magnesium:0.1 mol/L [<0.2 mol/L], an iron-magnesium mixture aqueous solution, iron:magnesium=1:1 molar ratio).

Comparison soil conditioner 3: a 1000 times diluted solution of said iron-magnesium mixture aqueous solution 3 prepared in COMPARISON 3 (iron, and magnesium were dissolved at the same time, iron:0.8 mol/L, magnesium:0.4 mol/L).

2. The Preparation of the Soil Sample and Comparison Soil Sample

Said soil conditioners 1 and 2, and Comparison soil conditioners 1, 2 and 3, (each 150 cc) were added to 5 L of soil on a paddy field for testing, and further, the proper amount of water was added to each, so as to adjust them, enabling the soil of each sample to be easily mixed. The resulting mixtures were then mixed sufficiently, and then kept separately for two weeks. Following this, said mixtures were each dried in the sun, and then each sieved with a 100 mesh sieve, to prepare minute soil samples.

Soil sample 1: treated with soil conditioner 1
Soil sample 2: treated with soil conditioner 2
Comparison soil sample 1: treated with comparison soil conditioner 1
Comparison soil sample 2: treated with comparison sail conditioner 2.
Comparison soil sample 3 treated with comparison soil conditioner 3.
Comparison soil sample 4*: treated with only water
* The Comparison soil sample 4 was a minute soil sample prepared by adding only water to the soil, and then treated by the same way as the other samples 3. Water Flow Test Each of 3 L of said soil samples, and said comparison soil samples was collected, after which each of the soil sample was filled into a cylinder, each cylinder having an outlet at its lower end. 2 L of water was poured into each cylinder at its upper end, after which the water flow conditions of each sample was observed.

As the evaluations of the water flow conditions, the water drop dripping start time (in minutes), wherein the water starts to drip from the lower end of the cylinder after the water has been poured into the cylinder, the permeation time (in minutes), wherein the water has completely permeated the soil after the water has been poured into the cylinder, and the water flow amount (the amount of water dripped), wherein the water has completely permeated soil after the water has been poured into the cylinder, were measured.

The results are shown in Table 16.

TABLE 16

| soil conditioner | water drop dropping start time (minutes) | permeation time (minutes) | water flow amount (ml) |
|---|---|---|---|
| soil conditioner 1 | 21 | 58 | 700 |
| soil conditioner 2 | 18 | 50 | 750 |
| comparison soil conditioner 1 | 32 | 86 | 370 |

TABLE 16-continued

| soil conditioner | water drop dropping start time (minutes) | permeation time (minutes) | water flow amount (ml) |
|---|---|---|---|
| comparison soil conditioner 2 | 28 | 63 | 440 |
| comparison soil conditioner 3 | 26 | 74 | 420 |
| comparison soil conditioner 4 | 40 | 126 | 200 |

Being based on Table 16, the ratios of the flow amount of the soil samples 1 and 2, each having been treated with the soil conditioners 1 and 2, and the flow amounts of the comparison soil samples 1, 2 and 3 having been treated with the comparison soil conditioners 1, 2 and 3, and the flow amount of the comparison soil sample 4, having been treated with only water, are shown in Table 17.

TABLE 17

| soil conditioner 1 | comparison soil conditioner 1 | 700/370 = 1.89 times |
| | comparison soil conditioner 2 | 700/440 = 1.59 times |
| | comparison soil conditioner 3 | 700/420 = 1.67 times |
| | comparison soil conditioner 4 | 700/200 = 3.5 times |
| soil conditioner 2 | comparison soil conditioner 1 | 750/370 = 2.03 times |
| | comparison soil conditioner 2 | 750/440 = 1.70 times |
| | comparison soil conditioner 3 | 750/420 = 1.79 times |
| | comparison soil conditioner 4 | 750/200 = 3.75 times |

Referring to Table 17, it is clear that the soils treated with the soil conditioners 1 and 2 of the present invention both have more than 1.5 times the flow properties as compared with the soils treated with the comparison soil conditioner 1 not containing magnesium, and the comparison soil conditioner 2 which was prepared using the single iron aqueous solution containing 0.3 mol/L of iron (<0.5 mol/L), and the single magnesium aqueous solution containing 0.1 mol/L of magnesium (<0.2 mol/L), and the comparison soil conditioner 3 which was prepared by mixing and dissolving iron and magnesium together at the same time. Accordingly, it is recognized that said soil conditioners of the present invention promote the formation of the soil's aggregate structure much more, than the comparison soil conditioners.

Further, when comparing the comparison soil sample 4 having been treated with only water, it is recognized that the soil that was treated with the soil conditioner of the present invention showed more than 3.5 times the flow amount than did the comparison soil sample 4 that was treated with only water, and further it is recognized that the soil samples that were treated with the comparison soil conditioners also showed a greater flow amount than the comparison soil sample 4.

EXAMPLE 18

Esthetic Effect

A fragrant lotion was prepared by diluting the iron-magnesium mixture aqueous solution 5 containing vitamin C in EXAMPLE 8, 1000 times with water.

Said fragrant lotion was applied onto the skin of a woman (34 years old) once a day, and after one month, the condition of her skin was observed. The result was that the appearance of wrinkles on her skin became superficial and that her skin appeared remarkably white and firm.

Further, as shown in FIG. 1 (photograph), a tightening effect of the facial akin could be recognized, the cheeks to jaw line of her face indicated by the dots appeared to become sharper than before the application of said fragrant lotion, while the slackening (bags) under her eyes appeared to dissolve, and the corners of her mouth appeared to turn upward. Overall, it was recognized that her face appeared tighter and smaller.

Figure 2:
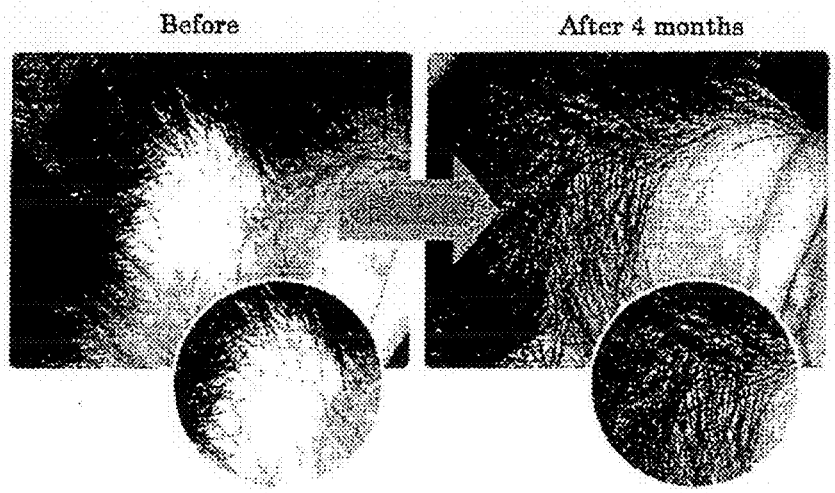
FIG. 2. A photograph illustrating the cosmetic effect achieved by using fragrant lotion containing said bioactive agent of the present invention.

Further, said fragrant lotion was applied onto the scalp of a woman (28 years old) once a day, and after four months the condition of her hair was observed. As a result, as shown in FIG. 2 (photograph), her hair appeared to have grown properly, around a bald spot, which had become less conspicuous.

POSSIBILITY OF INDUSTRIAL USE

The bioactive agent produced by the method of the present invention contains a stabilized ferrous iron salt and/or ferric ferrous iron salt with magnesium salt and as a result, the effect of the bioactive agent does not deteriorate when kept for a long period of time, the stabilized effect of its bioactivity being ensured. Accordingly the bioactive agent of the present invention is particularly useful as a cosmetic product, a freshness keeping agent, a growth promotion agent for plants and animals, a soil conditioner, and further, an original solution for medical use.

The invention claimed is:

1. A method for producing a bioactive agent comprising:
preparing an aqueous solution containing a ferrous iron salt and/or a ferric ferrous iron salt in a concentration of not less than 0.5 mol/L as iron in said ferrous iron salt and/or said ferric ferrous iron salt;
preparing an aqueous solution containing a magnesium salt in a concentration of not less than 0.2 mol/L as magnesium in said magnesium salt;
mixing the resulting aqueous solution of said ferrous iron and/or said ferric ferrous iron salt and the resulting aqueous solution of said magnesium salt;
then diluting the resulting iron-magnesium mixture solution into a prescribed concentration.

2. A method for producing a bioactive agent in accordance with claim 1, wherein the molar ratio of said ferrous iron salt and/or said ferric ferrous iron salt in the resulting iron-magnesium mixture is set to be in the range of between 1:0.05 and 1:1 as an iron-magnesium molar ratio.

3. A bioactive agent produced by a method comprising:
preparing an aqueous solution containing a ferrous iron salt and/or a ferric ferrous iron salt in a concentration of not less than 0.5 mol/L as iron in said ferrous iron salt and/or said ferric ferrous iron salt;
preparing an aqueous solution containing a magnesium salt in a concentration of not less than 0.2 mol/L as magnesium in said magnesium salt;
mixing the resulting aqueous solution of said ferrous iron and/or said ferric ferrous iron salt and the resulting aqueous solution of said magnesium salt;
then diluting the resulting iron-magnesium mixture solution into a prescribed concentration.

4. A bioactive agent, wherein one or more kind(s) of vitamin(s) selected from a group consisting of vitamins C, E and K is (are) added to said bioactive agent in accordance with claim 3, in an amount in the range of between 1 and $10^6$ moles per 1 mole of iron in said ferrous iron salt and/or said ferric ferrous iron salt.

5. A cosmetic product containing said bioactive agent in accordance with claim 3, wherein said cosmetic product is set to contain said bioactive agent in an amount in the range of between $5 \times 10^{-8}$ mol/L and $5.5 \times 10^{-6}$ mol/L as iron in said bioactive agent.

6. A freshness keeping agent containing said bioactive agent in accordance with claim 3, wherein said freshness keeping agent contains said bioactive agent in an amount in the range of between $5\times10^{-8}$ mol/L and $5.5\times10^{-5}$ mol/L as iron in said bioactive agent.

7. A growth promoting agent for plants and animals containing said bioactive agent in accordance with claim 3, wherein said growth promoting agent contains said bioactive agent in an amount in the range of between $5\times10^{-7}$ mol/L and $5.5\times10^{-5}$ mol/L as iron in said bioactive agent.

8. A soil conditioner containing said bioactive agent in accordance with claim 3, wherein said soil conditioner contains said bioactive agent in an amount in the range of between $5\times10^{-7}$ mol/L and $5.5\times10^{-5}$ mol/L as iron in said bioactive agent.

9. An original solution for medical use containing said bioactive agent in accordance with claim 3, wherein said original solution contains said bioactive agent in an amount in the range of between $2\times10^{-5}$ mol/L and $6\times10^{-3}$ mol/L as iron in said bioactive agent.

10. An original solution in accordance with claim 9, wherein said original solution is used as the original solution for prophylactics or therapeutics for cancer, diabetes, hepatitis, collagen disease, or atopic dermatitis.

11. A bioactive agent in accordance with claim 3, wherein the molar ratio of said ferrous iron salt and/or said ferric ferrous iron salt in the resulting iron-magnesium mixture is set to be in the range of between 1: 0.05 and 1:1 as an iron-magnesium molar ratio.

12. A bioactive agent, wherein one or more kind(s) of vitamin(s) selected from a group consisting of vitamins C, E and K is (are) added to said bioactive agent in accordance with claim 11, in an amount in the range of between 1 and $10^6$ moles per 1 mole of iron in said ferrous iron salt and/or said ferric ferrous iron salt.

13. A cosmetic product containing said bioactive agent in accordance with claim 11, wherein said cosmetic product is set to contain said bioactive agent in an amount in the range of between $5\times10^{-8}$ mol/L and $5.5\times10^{-6}$ mol/L as iron in said bioactive agent.

14. A freshness keeping agent containing said bioactive agent in accordance with claim 11, wherein said freshness keeping agent contains said bioactive agent in an amount in the range of between $5\times10^{-8}$ mol/L and $5.5\times10^{-5}$ mol/L as iron in said bioactive agent.

15. A growth promoting agent for plants and animals containing said bioactive agent in accordance with claim 11, wherein said growth promoting agent contains said bioactive agent in an amount in the range of between $5\times10^{-7}$ mol/L and $5.5\times10^{-5}$ mol/L as iron in said bioactive agent.

16. A soil conditioner containing said bioactive agent in accordance with claim 11, wherein said soil conditioner contains said bioactive agent in an amount in the range of between $5\times10^{-7}$ mol/L and $5.5\times10^{-5}$ mol/L as iron in said bioactive agent.

17. An original solution for medical use containing said bioactive agent in accordance with claim 11, wherein said original solution contains said bioactive agent in an amount in the range of between $2\times10^{-5}$ mol/L and $6\times10^{-3}$ mol/L as iron in said bioactive agent.

18. An original solution in accordance with claim 17, wherein said original solution is used as the original solution for prophylactics or therapeutics for cancer, diabetes, hepatitis; collagen disease, or atopic dermatitis.

* * * * *